United States Patent
Zikria

(10) Patent No.: US 6,564,101 B1
(45) Date of Patent: May 13, 2003

(54) ELECTRICAL SYSTEM FOR WEIGHT LOSS AND LAPAROSCOPIC IMPLANATION THEREOF

(75) Inventor: Bashir A. Zikria, Norwood, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/601,585
(22) PCT Filed: Feb. 2, 1999
(86) PCT No.: PCT/US99/02249
§ 371 (c)(1),
(2), (4) Date: Aug. 2, 2000
(87) PCT Pub. No.: WO99/38563
PCT Pub. Date: Aug. 5, 1999

Related U.S. Application Data

(60) Provisional application No. 60/073,421, filed on Feb. 2, 1998.

(51) Int. Cl.[7] .............. A61N 1/36; A61N 1/05
(52) U.S. Cl. ............................... 607/40; 607/133
(58) Field of Search .................. 607/40, 58, 133

(56) References Cited

U.S. PATENT DOCUMENTS

| | | | |
|---|---|---|---|
| 5,263,480 A | * 11/1993 | Wernicke et al. | 607/118 |
| 5,292,344 A | 3/1994 | Douglas | 607/40 |
| 5,423,872 A | 6/1995 | Cigaina | 607/40 |
| 5,690,691 A | 11/1997 | Chen et al. | 607/40 |
| 5,836,994 A | 11/1998 | Bourgeois | 607/40 |
| 5,861,014 A | 1/1999 | Familoni | 607/40 |

* cited by examiner

Primary Examiner—Carl Layno
(74) Attorney, Agent, or Firm—Reed Smith LLP

(57) ABSTRACT

An electrical device utilized to control the body weight of a medically overweight human being comprises of at least two electrical leads for implanting on the fundus of the stomach. An electrical generator/controller (pacemaker) generates and regulates the frequency and degree of electrical stimulation. The device can be used surgically, laproscopically, and/or endoscopically.

7 Claims, 2 Drawing Sheets

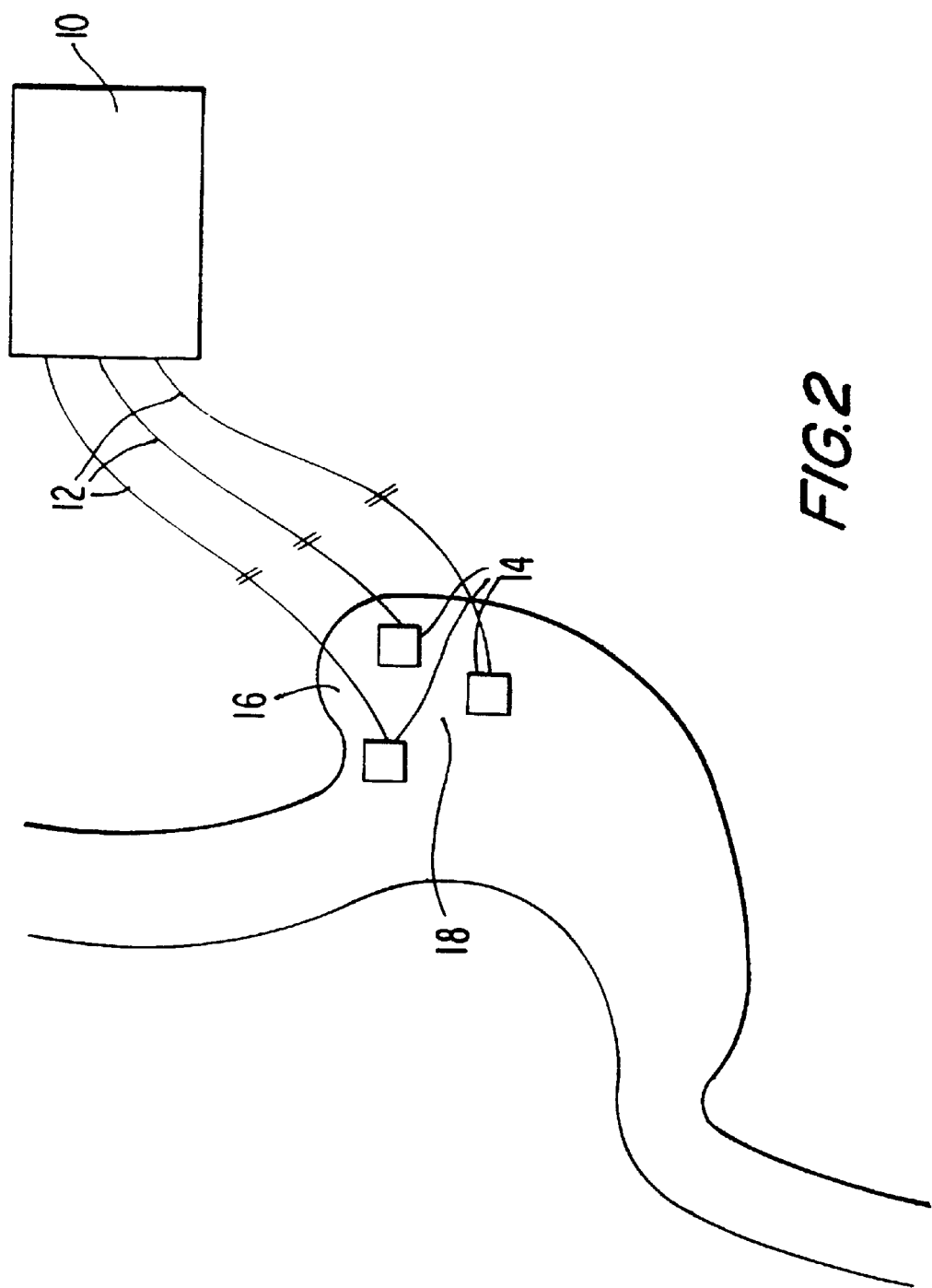

US 6,564,101 B1

ELECTRICAL SYSTEM FOR WEIGHT LOSS AND LAPAROSCOPIC IMPLANATION THEREOF

This application is a 371 of PCT/US99/02249 filed Feb. 2, 1999, which claims benefit of Provisional No. 60/073,421 filed Feb. 2, 1998.

FIELD OF THE INVENTION

The present invention relates generally to the field of weight loss devices and more particular to the field of electrical devices employed in the treatment of seriously overweight human beings.

BACKGROUND OF THE INVENTION

The treatment of obesity has taken many different forms. Among these is the use of prescription or non-prescription drugs or other ingestible preparations designed to suppress the appetite or to induce satiety. Another type of treatment comprises dietary menus selected to reduce caloric intake, often in combination with a regimen of exercise. In advance or extreme cases, the treatment of obesity has included more radical techniques such as stapling or re-sectioning of the stomach or wiring the jaws shut.

In general, these and other prior techniques for treating obesity have intended to produce only a temporary effect. After the initial weight loss and typical plateauing of further loss, the individual usually becomes discouraged and reverts to previous behavior. The more radical techniques employed for treating extreme cases are sufficiently drastic to warrant consideration of methods which are less intrusive and more easily tolerated by the patient.

A number of electrical devices and processes are known in the art for attempting to control an individual's food intake and/or various aspects of the digestive process in an effort to treat eating or digestive disorders. Wernicke et al., U.S. Pat. No. 5,188,104, discloses a method of detecting eating disorders and treating them by electrical stimulation of the vagus nerve, and Cigaina, U.S. Pat. No. 5,423,872, discloses a process and device for treating obesity and syndromes related to motor disorders of the stomach by altering the natural gastric motility of a patient by electrical stimulation to prevent emptying or to slow down food transit. Terry, Jr. et al., U.S. Pat. No. 5,540,730, discloses an apparatus and method of treating motility disorders by selectively stimulating a patient's vagus nerve to modulate electrical activity of the nerve and to thereby cause a selective release or suppression of excitatory or inhibitory transmitters One embodiment employs the manual or automatic activation of an implanted device for selective modulation. However, none of the aforementioned devices is totally satisfactory for effective treatment of eating disorders.

SUMMARY OF THE INVENTION

The present invention is directed to an electrical system to directly stimulate the stomach wall to create a sensation of satiety since normally distended "full stomach" stretch receptors of the stomach wall send the message of being full or satiated. More particularly, the present invention relies upon the use of implanted leads, similar to heart pacemaker leads, to directly stimulate the stretch receptors generally found in the wall of the upper portion, or fundus, of the stomach. The electrical stimulator leads (electrodes) are generally implanted using open or laparoscopic techniques and/or by endoscopic techniques with local anesthesia, thus making the effective utilization of the device of the present invention far easier and less burdensome to the patient than with the extensive major surgical procedures required using other known techniques.

A method for controlling the body weight of seriously overweight individuals which utilizes the system taught is also disclosed.

OBJECTS OF THE INVENTION

It is an object of the present invention to provide a novel electrical system for use in controlling the body weight of seriously overweight human beings.

It is also an object of the present invention to provide an electrical system for use in controlling the body weight of seriously overweight human beings which avoids the necessity of major surgical operations to make use of the system.

It is a further object of the present invention to provide an electrical system for use in controlling the body weight of seriously overweight human beings which may be easily deployed using laparoscopic or endoscopic techniques.

It is a yet further object of the present invention to provide an effective methodology for effecting the reduction in body weight of a seriously overweight individual using the electrical system taught here, which will be much less burdensome on the patient.

These and other objects of the invention will become apparent to one skilled in the art from the following more detailed disclosure of the invention.

BRIEF DESCRIPTION OF THE DRAWINGS

FIG. 2 is another schematic representation of the electrical system of the invention showing the leads implanted on the fundus of the stomach.

DESCRIPTION OF THE PREFERRED EMBODIMENT

Figure 1:
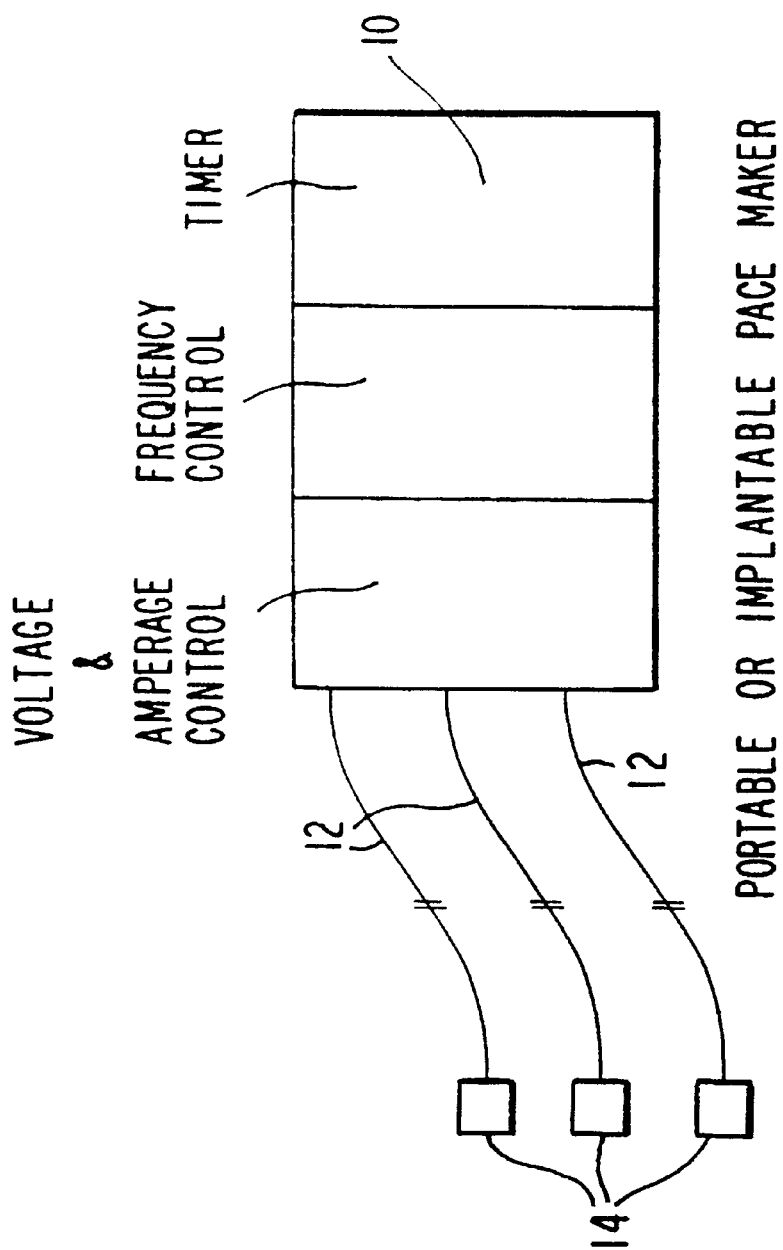
FIG. 1 is a schematic representation of an electrical system of the invention.

FIG. 1 is a schematic representation of one embodiment of the weight control system of the invention. An electrical signal generator/controller, or gastric pacer, 10 has two or more connecting wires 12, each one of which wires 12 terminates in an attachment lead 14. The number of connecting wires 12 and attachments leads 14 is variable and will depend upon various conditions and circumstances, such as the size of an individual's stomach and the degree to which the individual's appetite is to be suppressed. In its simplest form two leads (minimum) will be implanted on or in the stomach wall.

Pacer 10 may have conventional circuitry designed to generate low voltage, direct electrical pulses in the range of from about 50 millivolts to 10 volts, an amperage of from about 10 to 500 amps, a programmable pulse width of from about 0.1 to 10 msec, and a duration of from about 10 seconds to about 180 minutes, with possible use of constant output or ramped output stimulation. Preferably pacer 10 generates an electrical signal of from about 50 millivolts to about 5 volts, an amperage of from about 10 to 500 amps, and a pulse width of from about 0.1 to 1.0 msec for from about 10 seconds to about 120 minutes or more or substantially continuous low voltage stimulation with varying periodicity, in any case as a patient's specific physiology, anatomy, and/or psychology would require. Pacer 10 will preferably have a timing mechanism that will allow the timing and duration of the pulses to be varied or regulated as intended. For example, pacer 10 could be programmed to generate pulses of about 500 millivolts, an amperage of about 50 amps, and a pulse width of about 1 msec over 30 to 120 minutes for 2 or 3 preset times of the day. Alternatively, pacer 10 could be designed to provide an electronic electric pulse "on demand", that is, when activated by the individual and/or gastric wall contraction activated by hunger. In sum, there are effectively six parameters for the electrical signal, namely, voltage, amperage, pulse width, ramp, duration and periodicity.

Pacer 10 can also have a single pulse function. Preferably pacer 10 is located exterior to the patient on a halter or other supporting structure. Optionally, pacer 10 could be implantable subcutaneously or within muscle sheaths.

More specifically, pacer 10 could comprise a timer for periods of programmable stimulations during a 24 hour period, i.e., daily stimulations of the stretch receptors of the stomach, for the duration of the period of stimulation necessary to give the subject the feeling of satiety which may vary among subjects. Gastric pacers 10 may be clipped on a patient's belt, or implanted under the skin or muscle of abdominal area during the procedure. Such pacers, not unlike cardiac pacers, can be adjusted to the patient's needs by pacing system analyzers or pacemaker pulse monitors. Optionally more sophisticated programs can be applied to pacer 10 by a hand-held device (not shown) which, when positioned over the skin where pacer 10 is placed under skin or muscle, would have the capacity to effect changes in several parameters by radio frequency programming (i.e., changes in amperage, voltage, pulse width, frequency/min and periodicity/24 hr and ramping).

The source of the electrical power for pacer 10 is preferably one or more batteries to be located within the pacer. The pulse (gastric stimulation) generators would have batteries which could be replaceable or rechargeable. Optionally, pacer 10 could be electrically connected to a transformer or other power source, which may also be controlled by a transmitter with radio frequency 16. Also, hand-held device or another external device (not shown) may have the ability to recharge pacer 10.

In FIG. 2 the implantable leads are shown attached to the exterior wall of the stomach 16 in an area known as the fundus, or upper stomach wall. This area of the stomach is preferred since it is rich in stretch receptors. The leads can be implanted using anyone of a number of techniques, such as, for example, conventional surgery through a standard incision or laparoscopic surgery or under a local anesthetic. Obviously laparoscopic surgery would be preferred due to reduced trauma to the patient, potential complications, less hospital time, and overall less complications.

After implantation the generator/controller is activated, and stimulating electrical signals are sent to the leads, thereby effecting the stretch receptors located in the fundus of the stomach wall. Generator/controller 10 can be manually operated in an on/off mode or may be programmed to automatically generate an electrical signal over a period of time either in an intermittent or a continuous fashion.

It is contemplated that generator/controller 10 will be provided with means to program the device to allow it to generate electronic pulses at predetermined intervals. Similarly it is contemplated that the pulse generator/controller will be provided with means to program the device to allow it to generate electrical signals of varying intensities at various intervals over a predetermined time interval.

EXAMPLE

An adult male dog was fitted with a system according to the invention. Two implantable leads were implanted to the fundus of the dog's stomach. The implantable leads were connected by standard insulated copper wires to a generator/controller comprising a standard timing/pulsing controlled device. A 9V battery provided sufficient electrical charge.

On two occasions during a single day the subject animal was presented with a bowl of dog food. In each instance an electrical signal of 500 millivolts at pulse width of 0.5 to 1.0 milliseconds and frequency of 5 to 60 cycles was applied to the dog's stomach wall. When the signal was generated, the dog showed no interest in the food, and no food was consumed.

It will thus be seen that the objects set forth above, among those made apparent from the preceding description, are efficiently attained and, since certain changes may be made in the constructions set forth without departing from the spirit and scope of the invention, it is intended that all matter contained in the above description and shown in the accompanying drawings shall be interpreted as illustrative and not in a limiting sense.

What is claimed is:

1. A system for controlling the appetite of a medically overweight patient by sending electrical signals to the fundus of the patient's stomach, comprising:

an electrical signal controller;

at least one wire connector having distal and proximal ends, the proximal end being electrically connected to the controller; and at least one implantable attachment lead, one attachment lead being affixed to the distal end of each wire connector and each attachment lead being capable of being attached to the fundus of the patient's stomach, wherein the controller generates substantially continuous low voltage stimulation with varying periodicity as determined by the individual's specific physiology, anatomy or psychology, or a combination of two or more thereof.

2. The system of claim 1, wherein the controller is capable of being operated in continuous or intermittent manner.

3. The system of claim 1, wherein the controller is capable of being programmed to generate electrical signs to each implantable lead at predetermined intervals.

4. The system of claim 1, wherein the controller is capable of generating electrical signals of varying voltage and/or amperage at varying intervals over a predetermined time interval.

5. The system of claim 1, wherein the controller is also capable of varying the pulse width, ramp characteristics, duration, and/or periodicity of the electrical signals.

6. A method for controlling the appetite of a seriously overweight individual, comprising attaching one or more electrical leads to the fundus of the individual's stomach and activating a pulse generator/controller to stimulate stretch receptors found in the individual's stomach wall, wherein the pulse generator/controller generates substantially continuous low voltage stimulation with varying periodicity as determined by the individual's specific physiology, anatomy or psychology, or a combination of two or more thereof.

7. The method of claim 6, wherein the generator/controller generates an electrical signal of from about 50 millivolts to about 10 volts, an amperage of from about 10 to 500 amps, and a pulse width of from about 0.1 to 10 msec for from about 10 seconds to about 180 minutes or continuously.

* * * * *